(12) United States Patent
Bernate et al.

(10) Patent No.: US 9,597,692 B2
(45) Date of Patent: Mar. 21, 2017

(54) MICRO-FLUIDIC DEVICE FOR SORTING PARTICLES, AND METHODS FOR SORTING PARTICLES

(75) Inventors: Jorge A. Bernate, Baltimore, MD (US); Chengxun Liu, Leuven (BE); Liesbet Lagae, Leuven (BE); German Drazer, Baltimore, MD (US)

(73) Assignees: IMEC, Leuven (BE); Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/241,375

(22) PCT Filed: Aug. 27, 2012

(86) PCT No.: PCT/EP2012/066608
§ 371 (c)(1),
(2), (4) Date: Feb. 26, 2014

(87) PCT Pub. No.: WO2013/030155
PCT Pub. Date: Mar. 7, 2013

(65) Prior Publication Data
US 2014/0174994 A1    Jun. 26, 2014

Related U.S. Application Data

(60) Provisional application No. 61/527,853, filed on Aug. 26, 2011, provisional application No. 61/532,499, (Continued)

(51) Int. Cl.
*B03B 5/28* (2006.01)
*B01L 3/00* (2006.01)
*G01N 33/49* (2006.01)

(52) U.S. Cl.
CPC .......... *B03B 5/28* (2013.01); *B01L 3/502746* (2013.01); *B01L 3/502753* (2013.01);
(Continued)

(58) Field of Classification Search
CPC . B07B 5/00; B01L 3/502761; B01L 3/502753
See application file for complete search history.

(56) References Cited

U.S. PATENT DOCUMENTS

2007/0264705 A1    11/2007  Dodgson
2010/0300942 A1    12/2010  Sulchek et al.

FOREIGN PATENT DOCUMENTS

WO    2011/035185 A2    3/2011

OTHER PUBLICATIONS

International Search Report and Written Opinion, PCT International Application No. PCT/EP2012/066608, dated Feb. 6, 2013.

(Continued)

*Primary Examiner* — Luis A Gonzalez
(74) *Attorney, Agent, or Firm* — McDonnell Boehnen Hulbert & Berghoff LLP

(57) ABSTRACT

A method and device for the sorting and focusing of suspended particles is disclosed. The device has a micro-fluidic channel, at least one inlet and a number of outlets for providing, sorting and receiving particles. A patterned array of grooves is present inside the micro-fluidic channel. The inlets and outlets are connected to the micro-fluidic channel. The particles are sorted by the array of grooves. The method consists of providing particles in a flow-focused manner to one end of the micro-fluidic channel using at least one inlet. The particles are sorted by the array of grooves present in the micro-fluidic channel. Particles are collected by a number of outlets which are connected to the other end of the micro-fluidic channel.

24 Claims, 18 Drawing Sheets

Related U.S. Application Data filed on Sep. 8, 2011, provisional application No. 61/655,639, filed on Jun. 5, 2012.

(52) U.S. Cl.
CPC ...... *G01N 33/491* (2013.01); *B01L 3/502761* (2013.01); *B01L 2200/0652* (2013.01); *B01L 2200/0668* (2013.01); *B01L 2300/0816* (2013.01); *B01L 2300/0851* (2013.01); *B01L 2300/0864* (2013.01); *B01L 2400/086* (2013.01)

(56) References Cited

OTHER PUBLICATIONS

Chen, Hsiu-Hung et al., "Particle Enrichment Employing Grooved Microfluidic Channels", Applied Physics Letters, vol. 92, Apr. 28, 2008, pp. 173502-1-173502-3.
Mao, Wenbin et al., "Hydrodynamic Sorting of Microparticles by Size in Ridged Microchannels", Physics of Fluids, vol. 23, May 19, 2011, pp. 051704-1-051704-4.
Stroock, Abraham D. et al., "Chaotic Mixer for Microchannels", Science, vol. 295, Jan. 25, 2002, pp. 647-651.

Blood Cells

Blood cells*

| Cell | Density (g/cm³) | Blood count (no/μL) | Volume fl | Dimension (μm) | Unstressed shape |
|---|---|---|---|---|---|
| Erythrocytes Mature | 1.09 | 5 × 10⁶ | 87 | 8.5 × 2 | Biconcave disk, unnucleated |
| Reticulocytes⁺ | 1.07 |  |  |  | Irregular nucleated |
| Leukocytes |  | 30,000 | 300 | 8.5 × 5 | Wrinkle – surfaced sphere nucleated |
| Neutrophil |  | 4,200 | 440 | 9 × 4 |  |
| Eosinophil |  | 170 | 440 | 9 × 4 |  |
| Basophil |  | 50 | 440 | 9 × 4 |  |
| Lymphocyte |  | 2,200 | 210 | 7 × 4 |  |
| Monocyte |  | 460 | 460 | 9 × 5 |  |
| Platelets | 1.03 | 300,000 | 15 | 3 × 1 | Irregular disk |

*Adapted from Cokelet (1987)

⁺Reticulocytes are young blood cells that are just released from bone marrow. In patients with anemic condition, the reticulocytes count is often increased a reflection of the increased rate of red cell production.

Figure 18

MICRO-FLUIDIC DEVICE FOR SORTING PARTICLES, AND METHODS FOR SORTING PARTICLES

CROSS-REFERENCE TO RELATED APPLICATIONS

The present application is a U.S. national stage application of International Application Serial No. PCT/EP2012/066608 filed Aug. 27, 2012, which claims priority to U.S. Provisional Patent Application No. 61/527,853 filed Aug. 26, 2011, U.S. Provisional Application No. 61/532,499 filed Sep. 8, 2011 and U.S. Provisional Application 61/655,639 filed Jun. 5, 2012.

BACKGROUND OF THE INVENTION (a) Field of the Invention

The present invention is directed to the field of particle sorting in micro-fluidic devices.

(b) Description of Related Art

The simple and continuous micro-fluidic fractionation of the different components of a blood sample with high selectivity is a challenge. More generally speaking, the separation of the different constituents of a complex sample has been a subject of interest to the micro-fluidics community since the inception of the field, and a myriad of devices have been developed to accomplish this task. Some existing devices rely on external fields to exert a selective force on the different constituents of a sample. However, external components hinder the portability of the device, impose challenges such as high power consumption, and overall, increase their complexity. Other devices require a sieving matrix or some form of filtering, which makes them prone to clogging and limits their throughput.

In the separation of blood components, a common technique requires the chemical lysis of selective cells, which creates contamination and is particularly prone to introducing artifacts by altering the physiology of the enriched entities. The recirculation that ensues in these devices with confined geometries, in which the depth and width of the grooves is comparable to the height and width of the channel, has been used to effectively mix fluids at the micro-scale (Abraham D. Stroock et al., Chaotic Mixer for Microchannels, Science 295, 647 (2002)) (FIG. 1) and a lot of effort has been devoted to understand the properties of the helical flow above the grooves. Chen and Gao (Hsiu-Hung Chen and Dayong Gao, Particle enrichment employing grooved microfluidic channels, APL 92, 173502 (2008)]) used this recirculation to enrich particles by size in channels patterned with grooves, both channels and grooves having dimensions comparable to the dimensions of the particles (FIG. 2). However, less attention has been paid to the flow along the grooves.

Recently, Mao and Alexeev (Wenbin Mao and Alexander Alexeev, Hydrodynamic sorting of micro particles by size in ridged micro channels, POF 23, 051704 (2011)) carried out a computational study and showed that the flow along aligned slanted ridges patterned on the top and bottom surface of a straight channel can be used to deflect neutrally buoyant spherical particles to a different extent according to their size (FIG. 3). In their simulations, the separation between the ridges is larger than the radius of the particles, and inertial effects cause small particles to flow in the vicinity of the patterned surfaces and large particles to remain near the center of the channel. Thus, smaller particles are deflected by the flow along the grooves while larger particles are deflected in the opposite direction by the re-circulating flow.

SUMMARY OF THE INVENTION

According to a first aspect of the present invention, micro-fluidic device is disclosed for sorting particles in a liquid sample, the device comprising
 a micro-fluidic channel comprising a particle separation region comprising an array of grooves;
 a means for injecting the liquid sample into the micro-fluidic channel;
 a means for collecting particles whereby the means for injecting the liquid sample and the means for collecting particles are interconnected via the micro-fluidic channel, wherein the dimensions of the micro-fluidic channel are considerably larger than the dimensions of the grooves to prevent or reduce confinement effects.

According to preferred embodiments, the array of grooves is fully or partly patterned at the bottom surface of the micro-fluidic channel, and the non patterned part of the bottom of the surface is used to flow-focus the stream of particles.

According to preferred embodiments, the height of the micro-fluidic channel is at least 2 times the depth of the grooves.

According to preferred embodiments, the grooves are open-ended.

According to preferred embodiments, the height of the micro-fluidic channel is selected in order to reduce or avoid recirculation effects inside the micro-fluidic channel, the height being considerably larger than the depth of the grooves, the height being at least a multiple of the depth of the grooves, the multiple being at least 2, at least 3, at least 4, at least 5, at least 10, at least 15, at least 30 or at least 50.

According to preferred embodiments, the width of the channel is at least 50 times the width of the grooves.

According to preferred embodiments, the depth of each groove of the array of grooves is at least the size of the particles.

According to preferred embodiments, the distance between each groove of the array of grooves is at least the size of the particles.

According to preferred embodiments, the width and spacing between the grooves is at least 10 times the size of particles to be sorted.

According to preferred embodiments, the array of grooves are slanted and patterned at the bottom of the surface of the micro-fluidic channel. The array of grooves can be slanted and patterned only at the bottom of the surface of the micro-fluidic channel. The microfluidic channel can be open at the top. The microfluidic channel can be closed at the top or upper region, the upper surface which closes the channel on top being substantially unpatterned, and/or not comprising any ridges or grooves.

According to preferred embodiments, the grooves are oriented at an angle with respect to the main axis of the channel.

According to preferred embodiments, the means for injecting the liquid sample into to the micro-fluidic channel does so in a flow-focused manner.

According to preferred embodiments, the means for injecting the liquid sample comprises at least one inlet.

According to preferred embodiments, the means for injecting the liquid sample comprises an inlet and one or more micro-fluidic channels (inlets).

According to preferred embodiments, the means for collecting particles are one or more micro-fluidic channels, the channels being arranged to prevent recombining the segregated streams.

According to preferred embodiments, the channels are evenly spaced, thereby ensuring that they have the same hydrodynamic resistance.

According to preferred embodiments, the microfluidic device further comprises a sedimentation region arranged to let particles partly or fully sediment in order to diminish recirculation effects on the particles present above the array of grooves.

According to preferred embodiments, the method for sorting particles in a liquid sample with a device according to any of the embodiment of the first aspect is disclosed, the method comprising injecting the liquid sample into the micro-fluidic channel, separating particles with the separation region and capturing streams of different particles with the means for collecting particles.

According to preferred embodiments, the method comprises injecting the liquid sample into the micro-channel in a flow focused manner.

According to preferred embodiments, the method comprises allowing the sedimentation of the particles in the liquid sample before injecting the liquid sample into the micro-fluidic channel.

According to preferred embodiments, the method further comprises adjusting focusing and sample injection flow of one or more micro-fluidic channels for focusing the flow of particles.

According to a fifth aspect of the present invention, the use of a device, the device according to any of embodiments of the first aspect, for sorting particles in a liquid sample is disclosed, comprising flowing the liquid sample in the micro-fluidic channel at an average velocity which is comparable to the sedimentation velocity of the particles.

According to a sixth aspect of the present invention, the use of a device, the device according to any of embodiments of the first aspect, for sorting particles in a liquid sample is disclosed, comprising flowing the liquid sample in the micro-fluidic channel at an average velocity which is substantially larger than the sedimentation velocity of the particles.

BRIEF DESCRIPTION OF THE DRAWINGS

FIG. 18: Table illustrating density of different blood components.

DETAILED DESCRIPTION OF EMBODIMENTS

In aspects of this invention, advantage is taken of the flow characteristics in microfluidic devices in which the bottom surface is patterned with slanted rectangular grooves to continuously fractionate suspended particles based on their settling velocity. The flow is exploited in the vicinity of the patterned surface whereby the dimensions of the grooves are much smaller than the dimensions of the main channel to sort and focus particles with sizes smaller than the dimensions of the grooves.

The separation of particles put forth in embodiments of the present invention takes place in a straight micro-fluidic channel by flowing a suspension of particles with different sedimentation velocities over the vicinity of a surface patterned with a periodic array of shallow (compared to the height of the channel) rectangular grooves oriented at an angle with respect to the channel.

The grooves act as open channels guiding flow along them with the flow at the level of the top surface of the steps being in the direction of the main channel. The recirculation known to occur in this geometry is negligible in the vicinity of the patterned surface when the height and width of the channel is sufficiently larger than the depth and width of the grooves, respectively.

It was observed that the effect of a recirculation flow is suppressed by using large channels compared to the height of the ridges. The changing direction of the flow in the vicinity of the patterned surface can be exploited by fabricating ridges that are comparable in height to the dimensions of the particles being sorted.

In preliminary experiments, the height of the channel was 15 times larger than the depth of the grooves and no recirculation was observed. For a given flow rate, the width and depth of the grooves need to be large enough to allow the particles to sediment into the grooves. More precisely, the depth of the grooves needs to be at least comparable to the size of the particles while the width of the grooves needs to be long enough to allow the particles to settle into the grooves as they traverse them at a given speed. Thus, the separation of particles with sizes spanning all length scales from the molecular to the macroscopic is envisioned with the device and method presented in the current invention.

Figure 4:
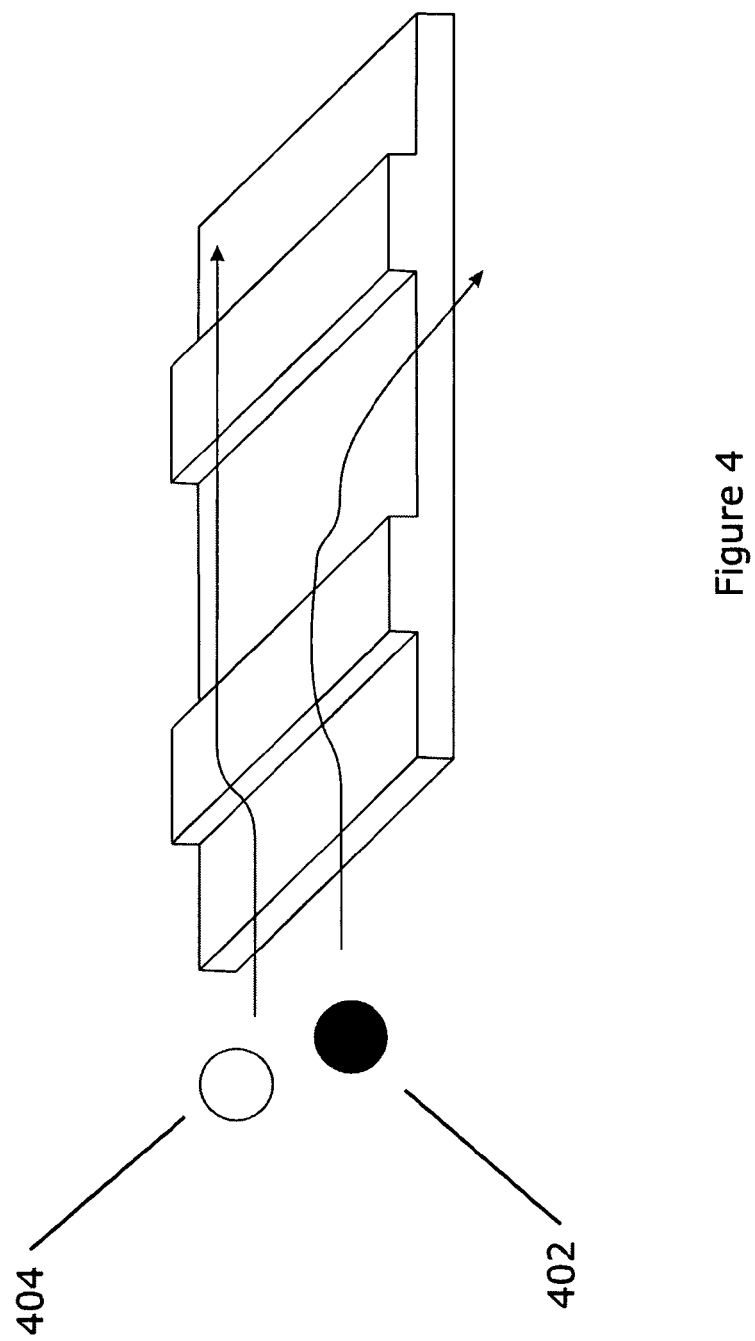
FIG. 4: Schematic of the separation principle. Trajectories of a light and a heavy particles are illustrated.

FIG. 4 shows a schematic of the separation principle. As the particles traverse the patterned surface, heavier particles 402 settle deeper into the grooves where the flow is predominantly along the grooves while lighter particles 404 do not settle and remain at heights for which the flow is predominantly in the direction of the main channel. Thus, heavier particles are deflected the most while the lighter particles are deflected the least.

The fractionation of the different components of a complex mixture is a crucial step in many clinical applications and in basic research. In particular, blood is a complex fluid having different specialized biological functions and containing a plethora of clinical information. A microfluidic platform has been developed for the passive and continuous fractionation of the different components of a suspension based on their settling velocity, and has been implemented to fractionate blood. In the present invention the different blood components are carried by a fluid flow over physical features patterned in the bottom wall of the device and are deflected laterally to a different extent based on their settling velocity. Specifically, the heavier red blood cells experience the largest deflection while the lighter platelets, white and rare blood cells deflect the least, allowing their passive and minimally invasive isolation. The methods allow the complete removal and recovery of red blood cells from the rest of the blood components and allows for the recovery of platelets and different subpopulations of white and rare blood cells. In addition, this fluidic platform can also be used to isolate specific targets, such us circulating tumor cells, leukocytes, bacteria, and bio-molecules, labeled with particles and using external fields to increase their settling velocity. A method and device for settling velocity based sorting and focusing of suspended particles using an array of grooves is disclosed.

In a first aspect of the invention, the present invention relates to a micro-fluidic device to sort particles suspended in a liquid sample. As will be understood by one of ordinary skill in the art, a liquid sample, in accordance with the present invention, includes but is not limited to body fluids such as blood and urine. The device (100) comprises a micro-fluidic channel (102) comprising a particle separation region (104) comprising an array of grooves (105), a means for injecting the liquid sample (101) into the micro-fluidic channel, a means for collecting particles (103) whereby the means for injecting the liquid sample (101) and the means for collecting particles (103) are interconnected via the micro-fluidic channel (102) whereby the dimension of the micro-fluidic channel is considerably larger than the dimensions of the grooves to prevent confinement effects.

Figure 7:
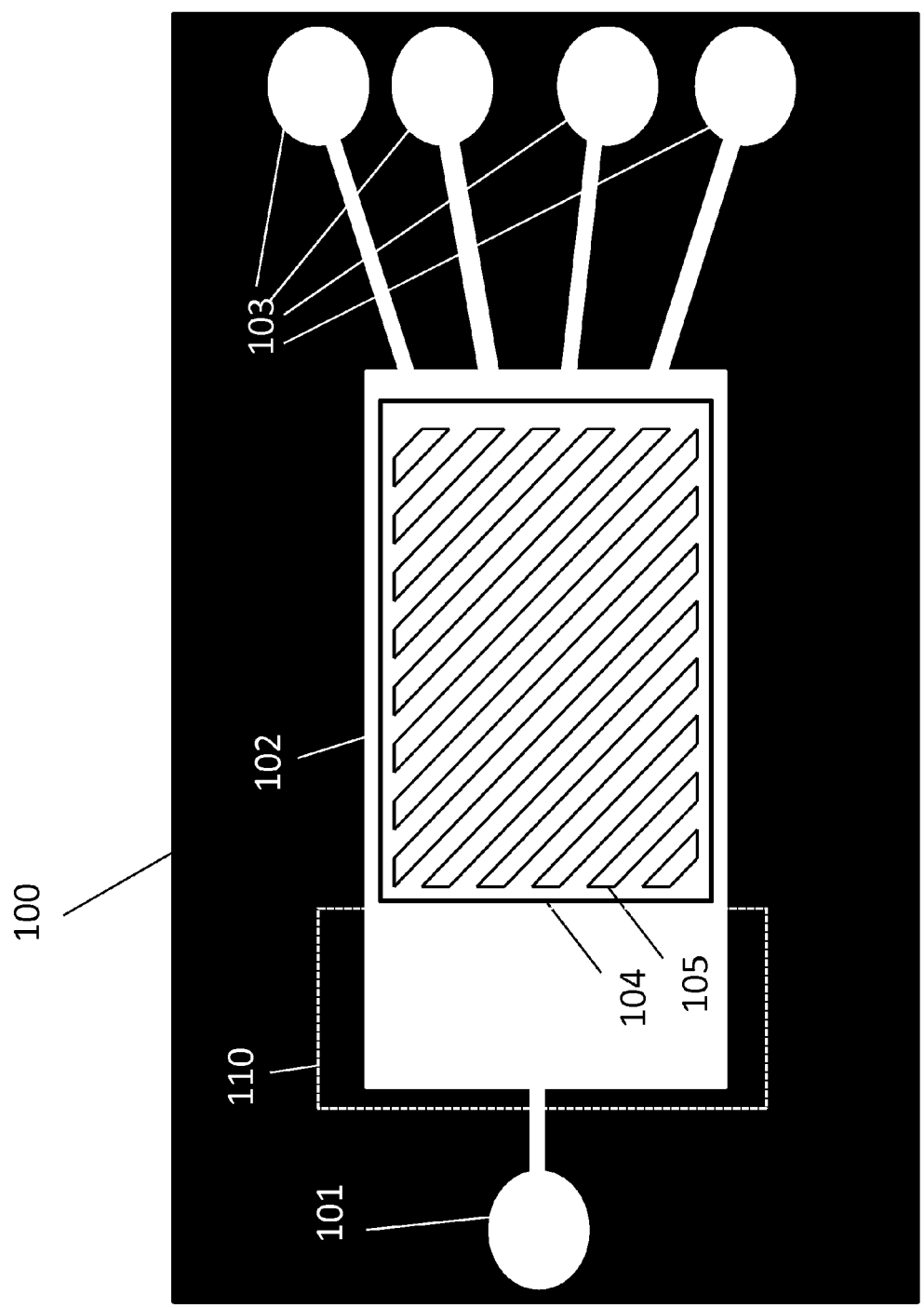
FIG. 7: Illustration of an embodiment of the device.

FIG. 7 is an illustration of such a device. It comprises one inlet (101) arranged to provide particles or liquid, a microfluidic channel (102), an array of grooves (105) patterned in the microfluidic channel (102) and a number of outlets (103) arranged to receive particles.

Generally speaking, the channel needs to be wide enough for the particles to separate laterally as they migrate in different directions. The width to height ratio of the main channel determines the extent of recirculation in the main channel. The wider the device, the higher the purity of the separated species.

In an embodiment of the first aspect of the invention, the distance between the top of the grooves and the top of the device are at least the size of the particles being sorted. The height of the grooves should be at least the size of the particles being sorted. The spacing between the grooves should be larger than the size of the particles being sorted. This way, that particles can enter the cavities created by the grooves.

Figure 6:
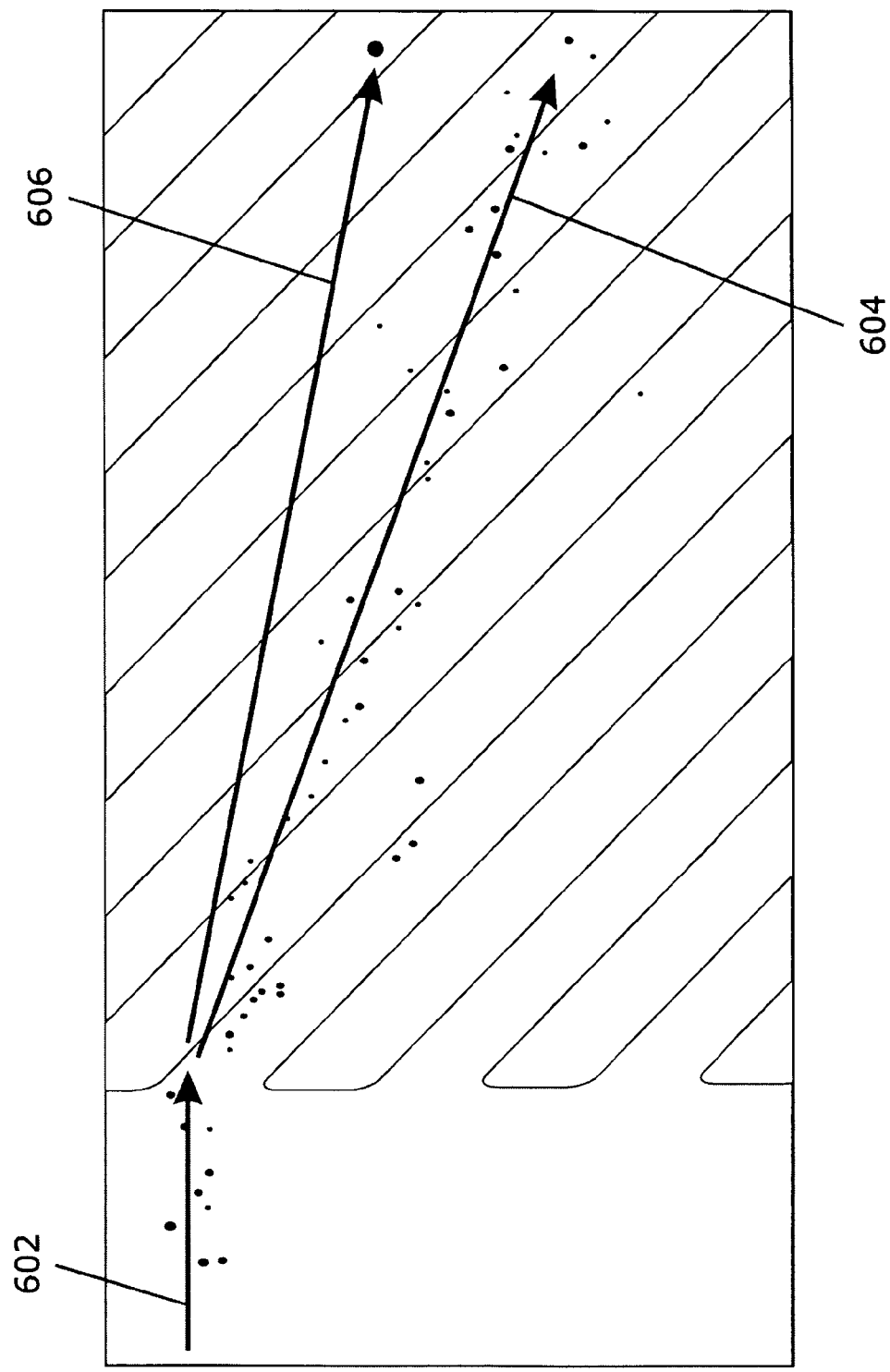
FIG. 6: Optical micrograph showing the separation of RBCs and of a cell distinctly larger than the RBCs, which could be a (lighter) leukocyte or a MCF-7 cell.

FIG. 6 shows an optical micrograph showing the separation of RBCs of a cell distinctly larger than the RBCs, which could be a (lighter) leukocyte or a MCF-7 cell. The darker stripes are protruding SU-8 features 20 microns tall with a width and spacing of 100 microns. The black arrow (602) indicates the direction of the flow-focused blood sample approaching the periodic array of grooves. The arrow (604) and arrow (606) indicate the direction of the RBCs and of a larger cell, respectively.

Figure 9:
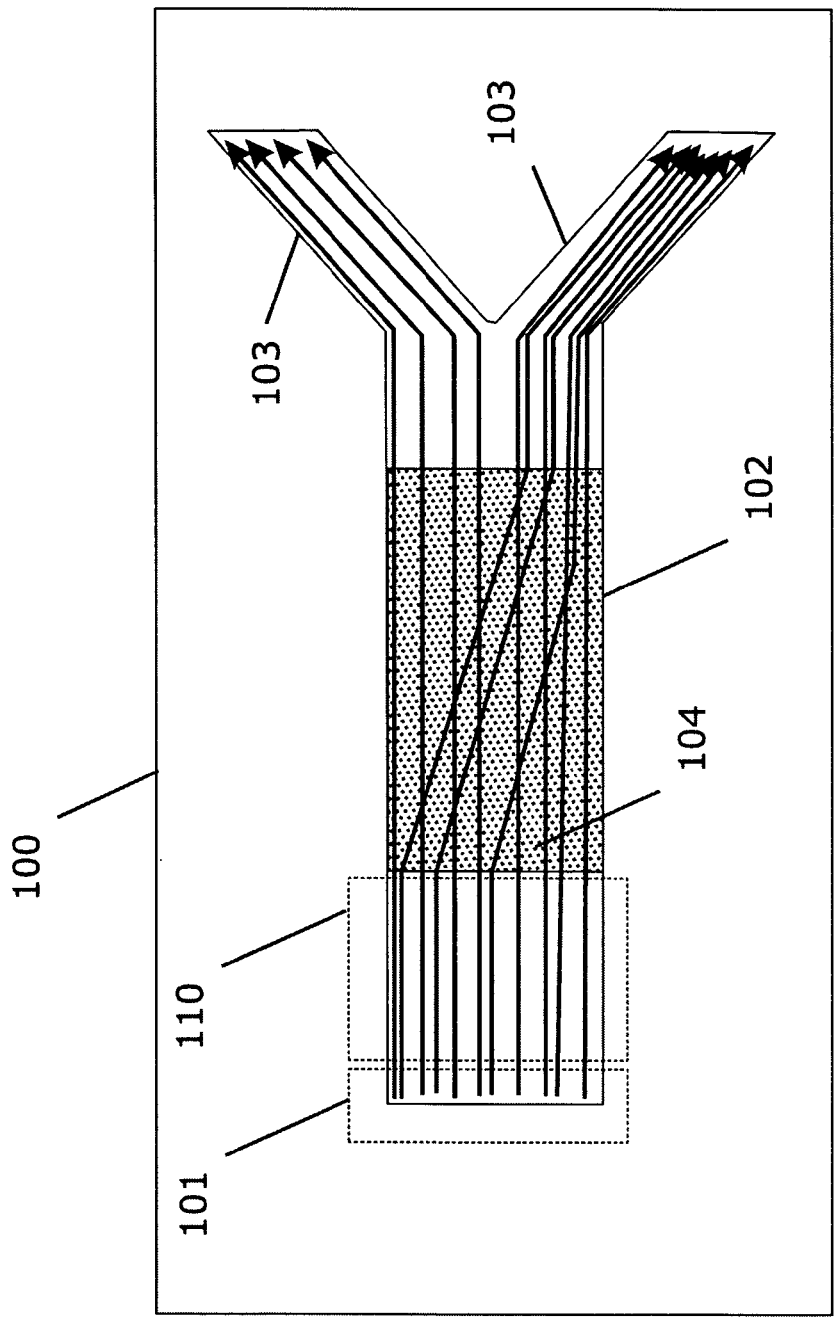
FIG. 9: Illustration of an embodiment of the device: enrichment-depletion.

FIG. 9 illustrates a device (100) comprising a micro-fluidic channel (102), a separation region (104) inside the micro-fluidic channel and a means for collecting particles (103). The separation region comprising an array of grooves (105).

In FIG. 9, a suspension of different particles is injected through a single inlet port in the micro-fluidic channel (102) with the particles reaching the separation region (104) distributed over the cross-section of the device. Particles that deflect are depleted from the left half of the device and enriched on the right half of the device. Thus, splitting the flow at the end of the device into two channels allows to continuously capturing the depleted and enriched streams.

In an embodiment of the first aspect of the invention, the particle separation region further comprises a sedimentation region (110) allowing the particles to sediment before entering the array of grooves. As an additional advantage, any recirculation effect that is still present in the micro-fluidic channel has less impact on the particles, allowing the particles to further sediment into the array of grooves instead of being influenced by the recirculation flow.

In an embodiment of the first aspect of the invention, the depth of the array of grooves is at least the size of the particles being sorted. As an advantage, the particles can be captured by the array of grooves.

The distance between each groove of the array of grooves is at least the size of the particles being sorted. This way, the particles are able to sediment into the grooves. In an embodiment of the first aspect of the invention, the array of grooves is fully or partly patterned at the bottom of the surface of the micro-fluidic channel whereby the non patterned part of the bottom of the surface may be used to flow-focus or sediment the stream of particles.

In an embodiment of the device the height of the micro-fluidic channel is 12.5 times the depth of the grooves, the width of the micro-fluidic channel is 420 times the width of the grooves. In another embodiment of the device the height of the micro-fluidic channel is 30 times the depth of the grooves, the width of the micro-fluidic channel is 840 times the width of the grooves. In another embodiment of the device the height of the micro-fluidic channel is 15 times the depth of the grooves, the width of the micro-fluidic channel is 50 times the width of the grooves and the width and spacing between the grooves is 10 times the size of particles and the grooves are oriented at an angle of 45 degrees with respect to the main axis of the channel.

The height of the micro-fluidic channel can be 5, 10 or 15 times the depth of the grooves, or can be at least 5 times or at least 10 times or at least 15 times, or at least 30 times or at least 50 times the depth of the grooves. The width of the channel can be 50 times, or 100 times or 200 times the width of the grooves. The width and spacing between the grooves can be 1, 2, or 5 or 10 times or 20 times of 30 times or 50 times the size of particles. The grooves can be oriented at an angle, different from 180° and 90°, with respect to the main axis of the channel. This angle can be for instance 30, 35, 40, 45, 50, 55, 60 degrees. The angle can be within the range of 20 to 70 degrees, or between 30 to 60 degrees. The main axis of the channel can be the longitudinal axis of the channel.

In an embodiment of the first aspect of the invention, the array of grooves (105) are slanted and patterned at the bottom of the surface of the micro-fluidic channel. The grooves serve to guide the flow responsible for the deflection of particles based on their settling velocity.

In an embodiment of the first aspect of the invention, the array of grooves (105) is fully or partly patterned at the bottom of the surface of the micro-fluidic channel whereby the non patterned part of the bottom of the surface is used to flow-focus the stream of particles.

In another embodiment of the first aspect of the invention, the means for injecting the liquid sample into to the micro-fluidic channel does so in a flow-focused manner. The means for injecting the liquid sample into the micro-fluidic channel can be adapted for focusing the flow of the sample.

In another embodiment of the first aspect of the invention, the means for injecting the liquid sample is an inlet.

In another embodiment of the first aspect of the invention the means for injecting the liquid sample comprises one or more inlets and one or more outlets.

In another embodiment of the first aspect of the invention the means for injecting the liquid sample comprises an inlet and one or more micro-fluidic channels (inlets).

In another embodiment of the first aspect of the invention the means for collecting particles are one or more micro-fluidic channels. The channels are arranged to prevent recombining the segregated streams. This is achieved by evenly spacing the channels and ensuring that they have the same hydrodynamic resistance.

In yet another embodiment of the first aspect of the invention, the device comprises at least one inlet and at least one outlet port, focusing region and a separation region which contains the grooves, a channel connecting the reservoir and the focusing region, flow-focusing channels, and collection ports. A sample can be injected into the at least one inlet, without injecting particles into the focusing and separation regions of the device, by closing the collection ports and opening the outlet port of the reservoir. After the particles have settled, the outlet of the reservoir is closed and the collection ports are opened to flow-focus a stream of the sample by adjusting the focusing and sample injection flows as required. As the particles exit the separation area of the device and flow towards the end of the channel, the separated bands of particles can be continuously captured in different collection ports.

In another embodiment of the first aspect of the invention, the means for injecting the liquid sample into the micro-fluidic channel does so in a flow-focused manner. As an additional advantage, the particles are not scattered over the micro-fluidic channel and can be sorted after segregating into different bands in the separation region of the micro-fluidic channel.

In another embodiment of the first aspect of the invention, the means for injecting the liquid sample is a single inlet.

In another embodiment of the first aspect of the invention the means for injecting the liquid sample comprises a sedimentation region, for instance a sedimentation or settling reservoir comprising one or more inlets and one or more outlets. As an additional advantage, this sedimentation region is used to settle particles before injecting them into the separation region of the micro-fluidic channel. A sedimentation region is a region which allows sedimentation of particles in a liquid flow to be injected or introduced as a flow in a particle separating region.

In another embodiment of the first aspect of the invention the means for injecting the liquid sample comprises an inlet (106) and one or more micro-fluidic channels (inlets) (107).

Figure 10:
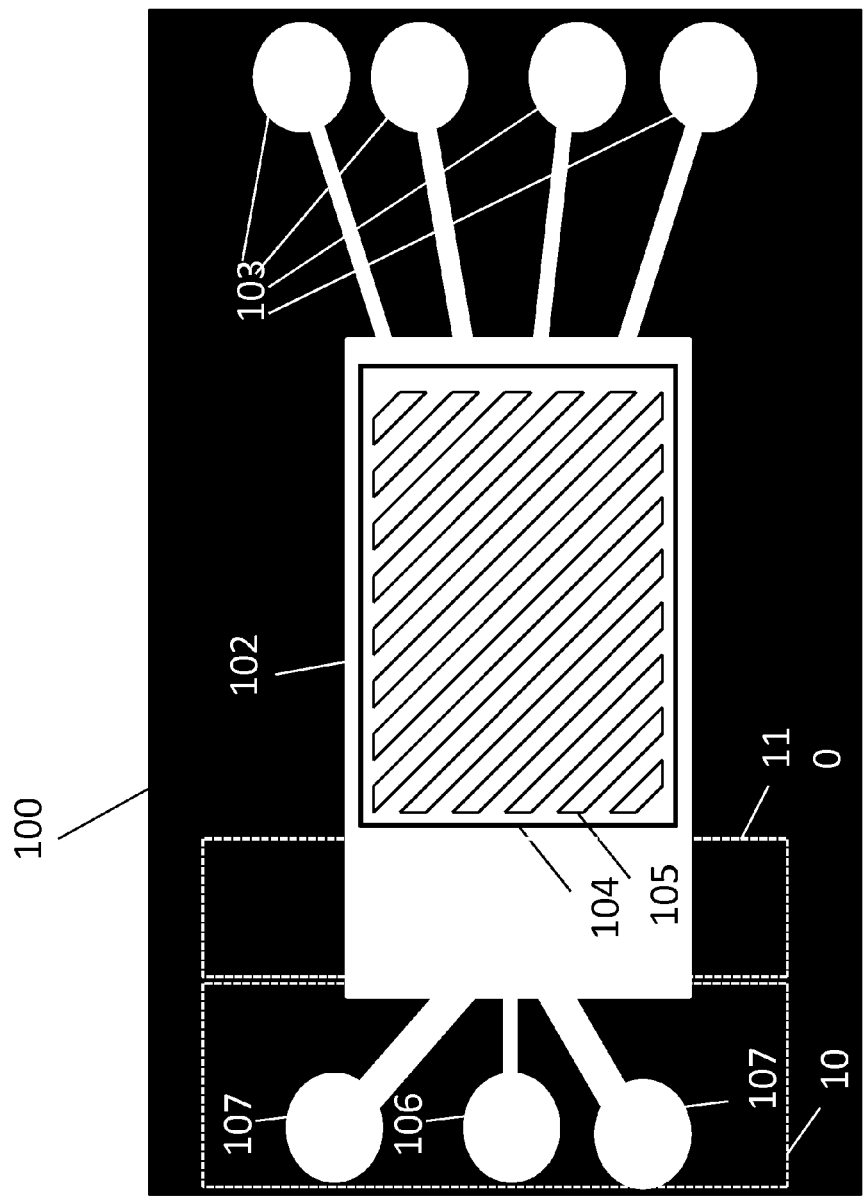
FIG. 10: Illustration of an embodiment of the device comprising multiple inlets, a sedimentation region used for sedimenting particles and flow focusing particles, an array of grooves for separating particles and multiple inlets for receiving particles.

As an additional advantage, the flow of the one or more micro-channels are used to focus the stream of particles. This is achieved by adjusting the focusing and sample injection flows of these micro-channels. FIG. 10 illustrates such an embodiment. The means for injecting the liquid sample (101) comprises 3 inlets: One inlet (106) is used for injecting the liquid sample, 2 inlets (micro-fluidic-channels) (107) are used to flow-focus the stream of particles coming from the inlet (106).

Figure 8:
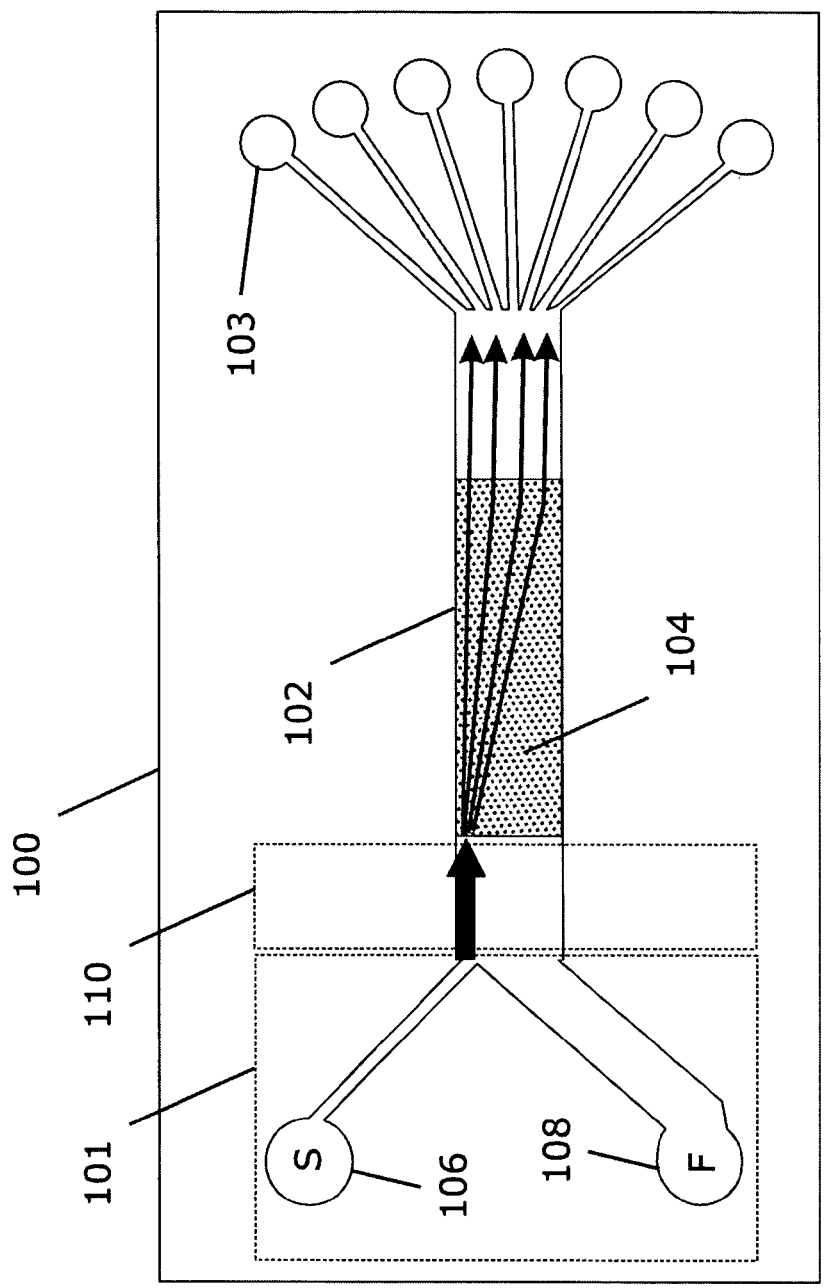
FIG. 8: Illustration of an embodiment of the device: vector separation of the different components of a mixture.

FIG. 8 is another illustration of such an embodiment. The means for injecting the liquid sample (101) comprises 2 inlets (108 & 106). The embodiment further comprises a micro-channel (102) with a separation region (104) and a means for collecting particles (103).

In FIG. 8, the liquid sample is injected through the inlet labeled "S" (106) and focused with a particle-free stream injected through the inlet labeled "F" (108). The separation region (102) of the micro-fluidic channel comprises the array of grooves, supposed to be slanted to the right, patterned at the bottom surface of the channel. The different components of the sample (represented by lines of different color) deflect to a different extent based on their settling velocity. The separated streams of particles can be continuously captured through the different collection ports (103) at the end of the micro-fluidic channel.

In another embodiment of the first aspect of the invention the means for collecting particles are one or more micro-fluidic channels. The channels are arranged to prevent recombining the segregated streams. This is achieved by evenly spacing the channels and ensuring that they have the same hydrodynamic resistance.

In a second aspect of the invention, the present invention relates to a method for sorting particles in a liquid sample with a device as described in the first aspect of the invention. The method comprises injecting the liquid sample into the micro-fluidic channel, separating particles with the separation region and capturing streams of different particles with the means for collecting particles.

In an embodiment of the second aspect of the invention, injecting the liquid sample into the micro-channel is performed in a flow-focused manner.

In an embodiment of the second aspect of the invention, the method as described above further comprising adjusting focusing and sample injection flow of one or more micro-fluidic channels for focusing the flow of particles.

In a third aspect of the invention, the present invention relates to a micro-fluidic device for focusing particles in a liquid sample. The device (109) comprises a micro-fluidic channel (102) comprising a particle focusing region (104) comprising an array of grooves (105), a means for injecting the liquid sample (101) into the micro-fluidic channel, a means for collecting particles (103) whereby the means for injecting the liquid sample and the means for collecting particles are interconnected via the micro-fluidic channel (102) and whereby the bottom surface of the micro-fluidic channel is patterned with an array of grooves (105), each having an inverted V-shape.

As an additional advantage, for focusing particles, the flows along the oppositely oriented branches of the inverted V-grooves focus the particles towards the point where these flows converge.

Figure 11:
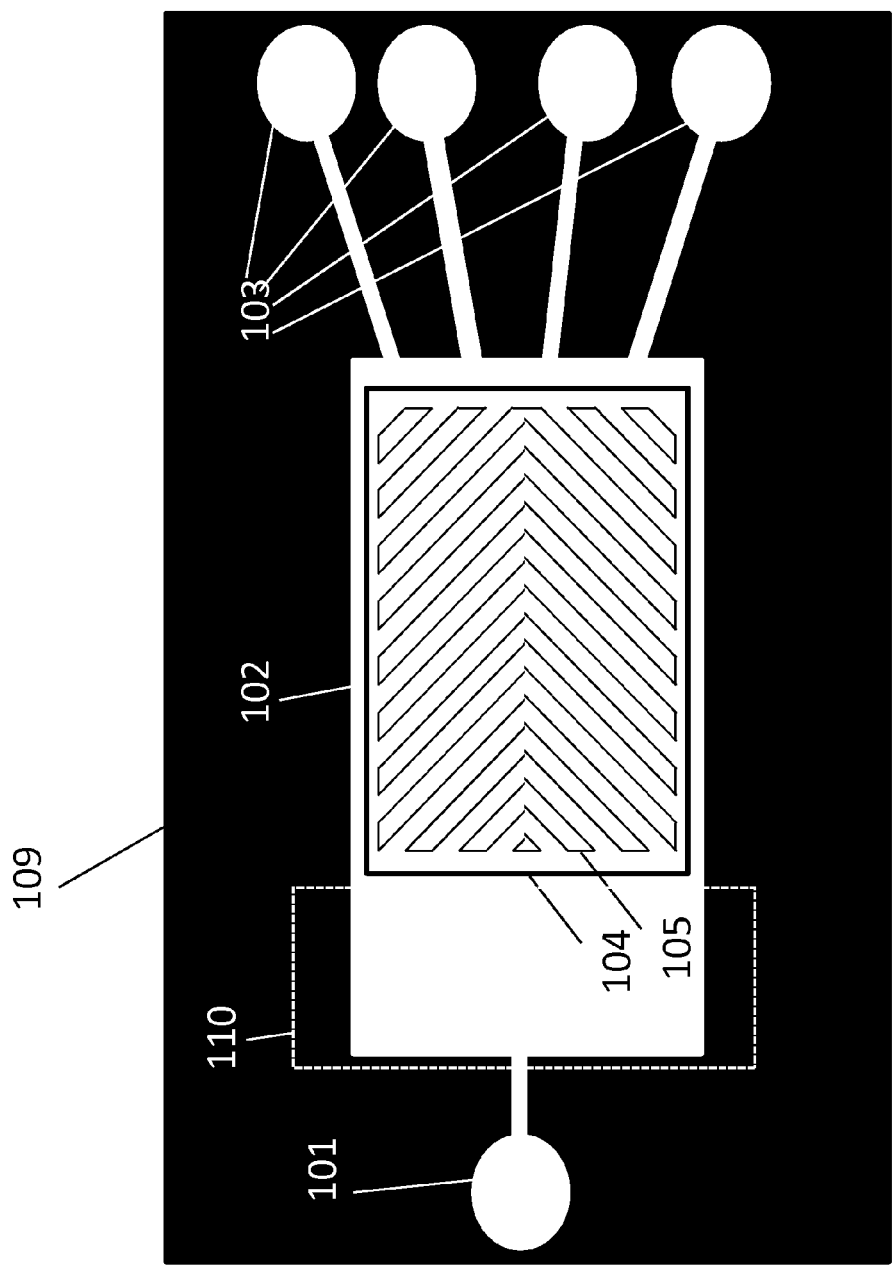
FIG. 11: Illustration of an embodiment of the device with V-shaped grooves to focus particles.

FIG. 11 is an illustration of such a device.

In a fourth aspect of the invention, the present invention relates to a method for focusing particles in a liquid sample with a device as described in the third aspect of the invention. The method comprises injecting the liquid sample into the micro-fluidic channel (102), and focusing particles with the particle focusing region (104).

In a fifth aspect of the present invention, the use of a device according to the first aspect of the present invention for sorting particles in a liquid sample is disclosed, comprising flowing the liquid sample in the micro-fluidic channel at an average velocity which is comparable to the sedimentation velocity of said particles. This is preferably used when the aim is to sort particles based on their mass. The average velocity can for instance be within a 30%, or within a 25%, or within a 20% or within a 15%, or within a 15% or within a 10% variation of the sedimentation velocity.

In a sixth aspect of the present invention, the use of a device according to the first aspect of the present invention for sorting particles in a liquid sample is disclosed, comprising flowing the liquid sample in the micro-fluidic channel at an average velocity which is substantially larger than the sedimentation velocity of the particles. This is preferably used when the aim is to sort particles based on their size. The average velocity can for instance be more than 150% or more than 200% or more than 500% or more than 1000% of the sedimentation velocity.

In the following section, a description of the fabrication methods and procedures pertaining to proof-of-concept blood fractionation experiments will be given.

IMPLEMENTATION AND EXPERIMENTAL RESULTS

Experimental Set 1

Device Design and Fabrication

Figure 5:
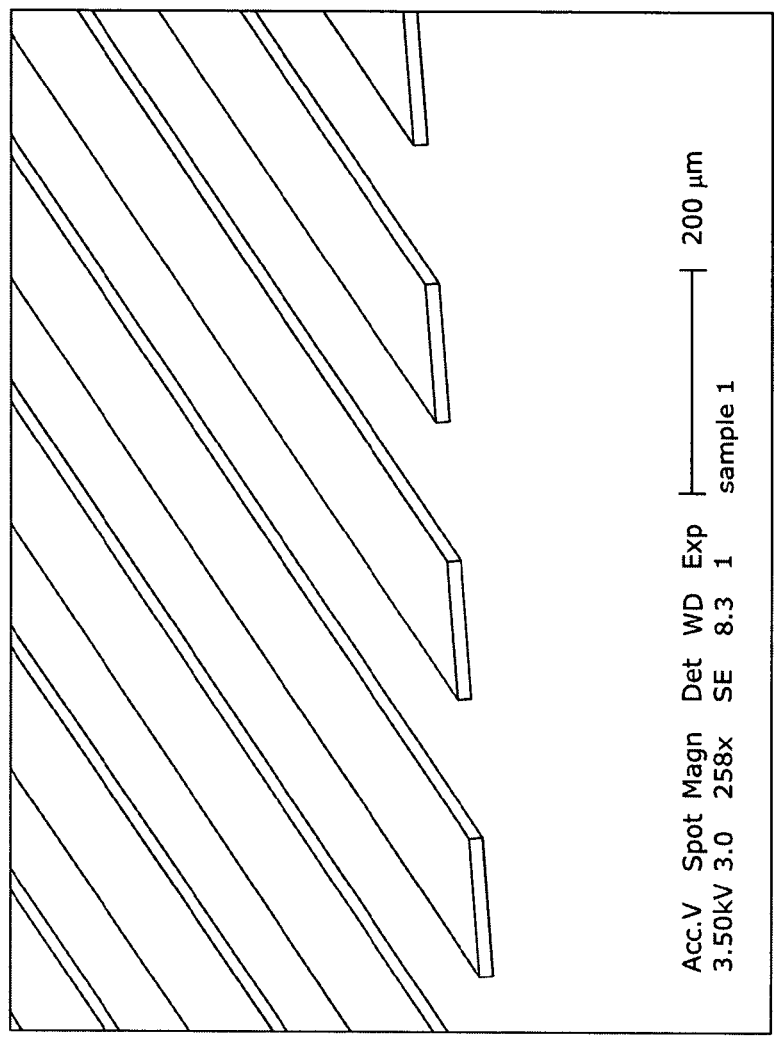
FIG. 5: SEM image of a silicon wafer patterned with SU-8 features that create a periodic array of grooves.

In our experiments, the fluidic channels were made out of PDMS using a standard molding and casting procedure. In short, a mold was made on a silicon wafer using standard photolithography with the negative resist SU-8 2150 to give features 400 microns tall. A PDMS negative replica was then casted using this mold. The patterned surface consists of a silicon wafer patterned (using standard photolithography) with a periodic array of protruding SU-8 2025 rectangular stripes 20 microns tall and with a width and a spacing between stripes of 100 microns (FIG. 5). Note that grooves carved into the, instead of protruding out, the surface could give an equivalent geometry. The device is sealed by irreversibly bonding the PDMS fluidic layer with the patterned silicon wafer after activating both surfaces with oxygen plasma. Such a device could be made via many other standard micro-fabrication techniques such as injection molding, micromachining, and using a variety of other materials including different polymers, glass, and other photo-resists.

Figure 1:
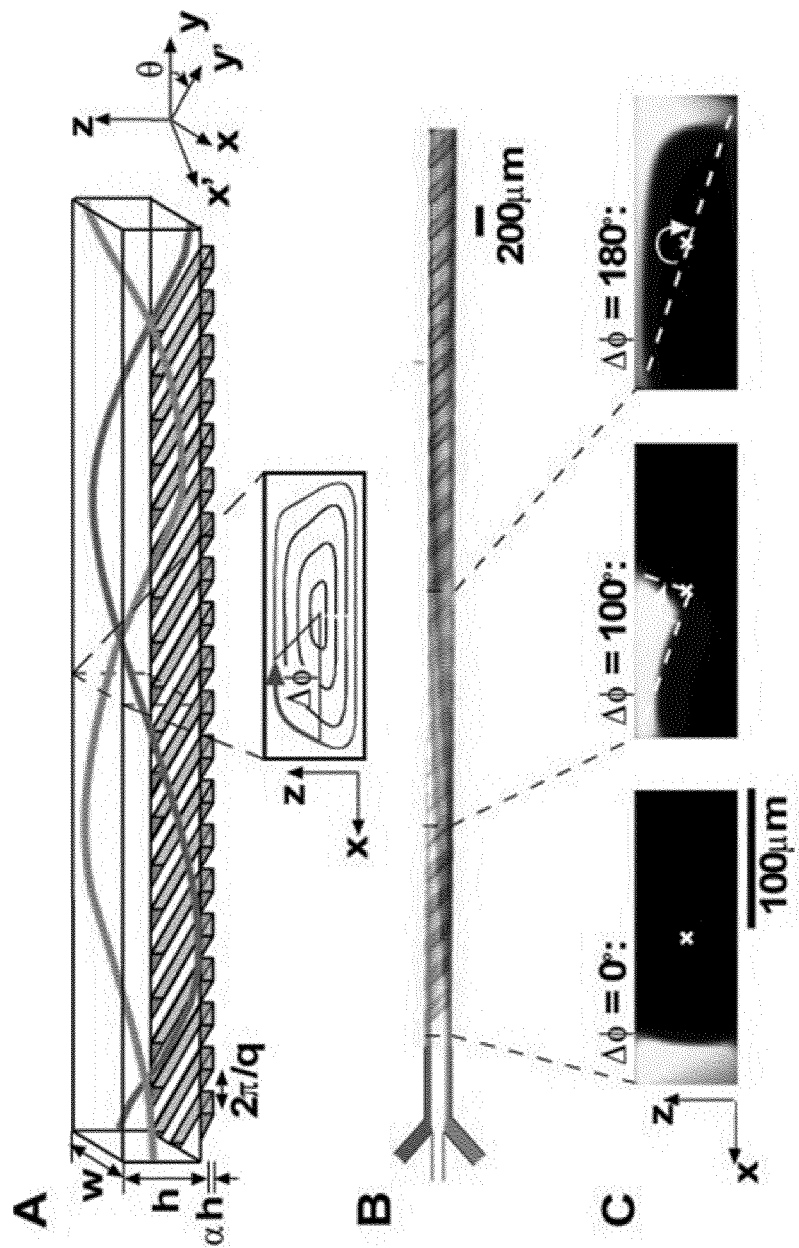
FIG. 1: (prior art) Slanted grooves patterned on one of the surfaces of a micro-fluidic device.

Sample Preparation, Device Pretreatment, Sample Injection, Microscopy and Data Collection In our proof-of-concept blood fractionation experiments, 10 μL of a freshly drawn blood sample were diluted in 1 mL of Dulbecco's Modified Eagle Medium and spiked with MCF-7 breast cancer cells. Prior to the injection of the diluted blood, the device was purged with ethanol and DI water, treated with PEG 4000 and finally flushed with medium. The blood sample was flow-focused to give the settled red blood cells a speed of approximately 100 microns/sec in the focusing region. Images of the blood cells approaching and traversing the array of grooves were captured at a rate of at least 4 fps using an upright microscope equipped with a digital camera. FIG. 1 shows the separation of a large cell, which could be a large leukocyte or an MCF-7 cell, form a stream of RBCs. It is observed in the experiments that the heavier red blood cells (RBCs) deflect the most while the lighter platelets, white blood cells (WBCs) and MCF-7 cells deflect the least (Densities of different blood components is given in FIG. 18). It is also observed that the deflection of different populations is not monotonic with particle size and depends on the flow rate. These observations suggest that the settling velocity is the factor controlling the extent of the deflection of different particles.

Experimental Set 2

Device Design and Fabrication

Figure 12:
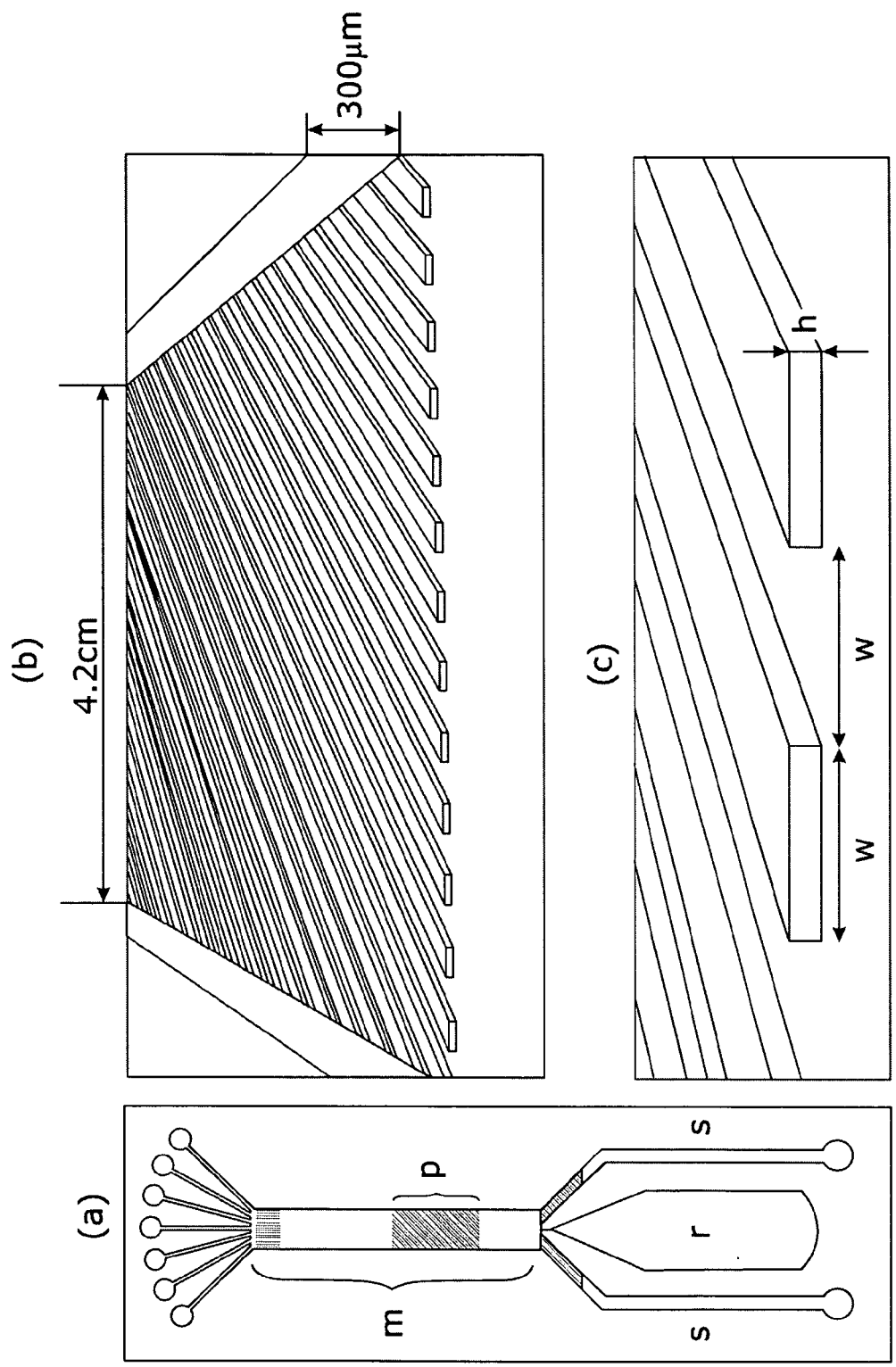
FIG. 12: Illustrates a particular embodiment of the device.

Fluidic channels were made out of PDMS using a standard molding and casting procedure. In short, a mold was made on a silicon wafer using standard photolithography with two layers of the negative photoresist SU-8 3050 (Microchem) to give features 300 microns tall. A PDMS negative replica was then casted using this mold. The patterned surface consists of a microscope glass slide (1 slide (1 with two layers of the negative photoresist SUnol anphotoresist SU-8 3025 (Microchem)] with a periodic array of protruding rectangular ridges. The device was sealed by irreversibly bonding the PDMS fluidic layer with the patterned glass slide after activating both surfaces with oxygen plasma. FIG. 12(a) shows a top-view schematic of the device; sheath flows from the side channels (s) allowed to flow focus particles and cells from the settling reservoir (s) into the main channel (m) and towards the patterned region (p) (also shown in perspective view in FIG. 12(b)). Experiments were performed with two different devices with the same dimensions for the fluidic layer and patterned region but with ridges of different height and width [h=10 μm, w=50 μm and h=24 μm, w=100 μm mw=100 412(c)=1

Sample Preparation, Device Pretreatment, Sample Injection, Microscopy and Data Collection The fluids [DI water and 0.5% bovine serum albumin (BSA) in phosphate buffer saline (DPBS, Gibco, life technologies) for the particles and blood experiments, respectively] was pumped through the device using a pressure-driven flow system. Each inlet was pressurized using a 0-5 psi regulator and was equipped with a switching valve (IDEX health & science) that was used to route the fluid to the device either from the pressurized containers or from a syringe. The syringes were used to prime and clean the device between experiments. The device was first flushed by manually injecting 5 mL of 5% Alconox detergent in DI water through each of the three inlets. If necessary, the device was sonicated while being flushed to remove adhered material. For the particle experiments, the device was simply flushed with the same volume and in the same way with DI water. For the blood experiments, the device was similarly flushed with water, then with DPBS, and finally with 2.5% BSA in DPBS. The device was then left blocking overnight on crushed ice. Prior to the injection of the blood sample, the device was flushed with 0.5% BSA. After priming and pretreatment, the device was mounted on an upright transmitted light microscope for the particle experiments and on an inverted phase contrast microscope for the blood experiments. The samples were manually injected into the settling reservoir immediately after preparation. The cells were let sediment until no more RBCs and WBCs were observed to arrive at the bottom surface of the settling reservoir, for no more than 15 mins (platelets were still distributed over the height of the device). WBCs, RBCs, and platelets could be readily distinguished under the phase contrast microscope without the need of fluorescence dyes. Platelets are clearly smaller than the rest of the blood cells. WBCs appear round and do not change shape and brightness considerably as they flow. In contrast, stationary RBCs appear dark in the center of the disk and bright in the surrounding area. Moreover, RBCs exhibit different modes of motion and the center of the disk and brigh speeds. At high velocities, however, RBCs align with the flow and appear as bright ellipsoids of constant intensity. Videos of the particle and cells were captured in middle of the cross-section of the device in the plain region as they approached the patterned area and about 1 mm into the patterned area to measure the approach velocity and the deflection angle (the difference between the approach angle and migration angle of the cells on the patterned region).

Results

Figure 13:
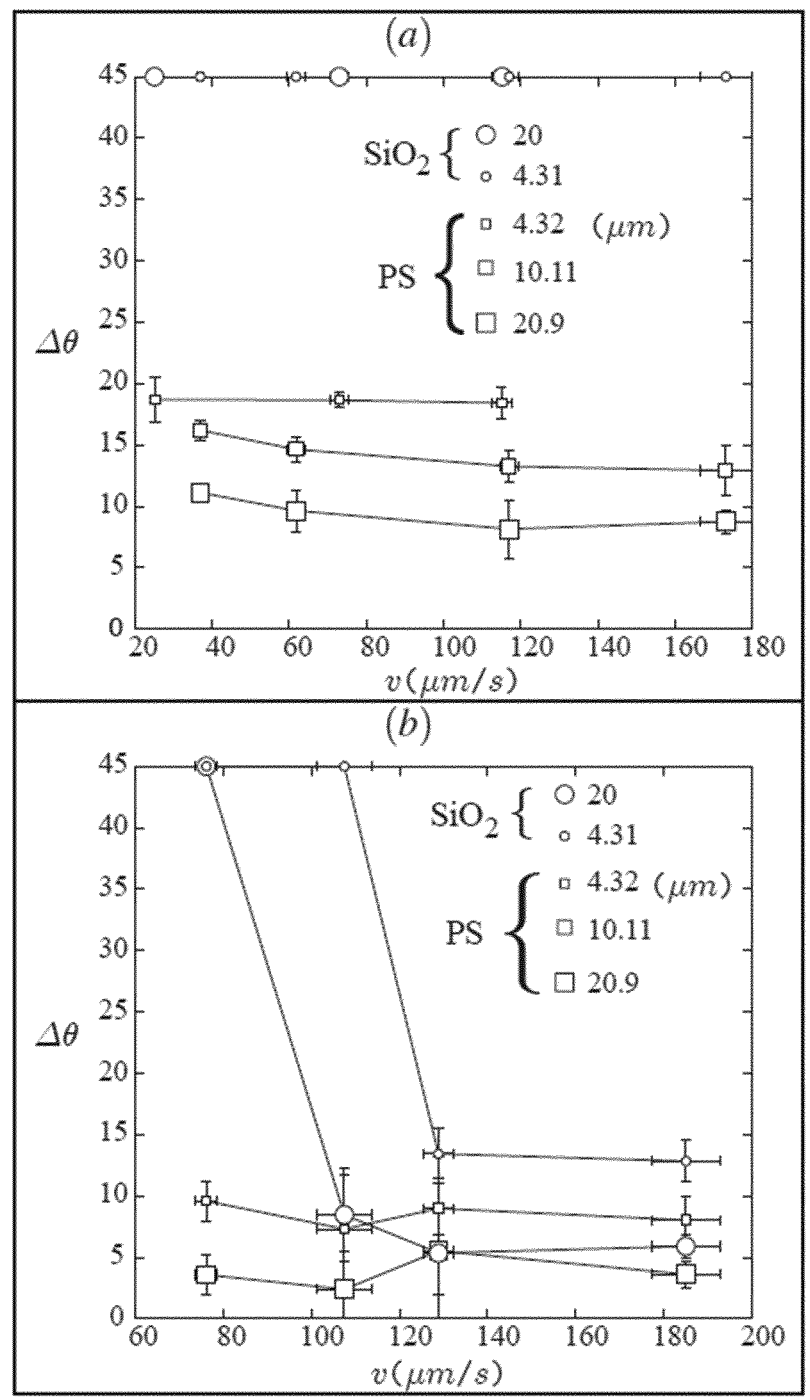
FIG. 13: Illustrates the deflection angle for two embodiments of the device with different feature geometries.

In this section, the behavior of spherical particles of different size and density is discussed. Specifically, experiments with silica (SiO2) particles of 4.3 and 20 µm diameter and polystyrene (PS) particles of 4.3, 10, and 20 µm diameter were carried out. FIG. 13 show the deflection angle for the two different feature geometries considered here, corresponding to large (24 µm tall by 100 µm wide) [FIG. 13(a)] and small (10 µm tall by 50 µm wide) [FIG. 13(b)] ridges, both oriented 45 degrees with respect to direction of the main channel. In both figures, the velocity of the 4.3 µm silica particles in the flat region of the device (before the slanted ridges) is used to characterize the flow velocity. Note that these particles are present in all the experiments and provide a good basis for comparison. In FIG. 13(a) it is observed that all the silica particles (4.3 and 20 µm) are confined to flow along the cavities for all the flow velocities considered here, corresponding to $\Delta\theta=45$ degrees. In contrast, PS particles can easily move over the ridges and exhibit substantially smaller deflection angles compared to silica particles. The SiO2 particles are confined to flow along the cavities over the range of velocities considered ($\alpha=45°$) for the large ridges, but are able to eventually go over the small ridges. PS particles can easily traverse the cavities and deflect to a less extent i) as their size increases for a given geometry of the ridges and ii) for the smaller ridges for a given particle size.

Figure 14:
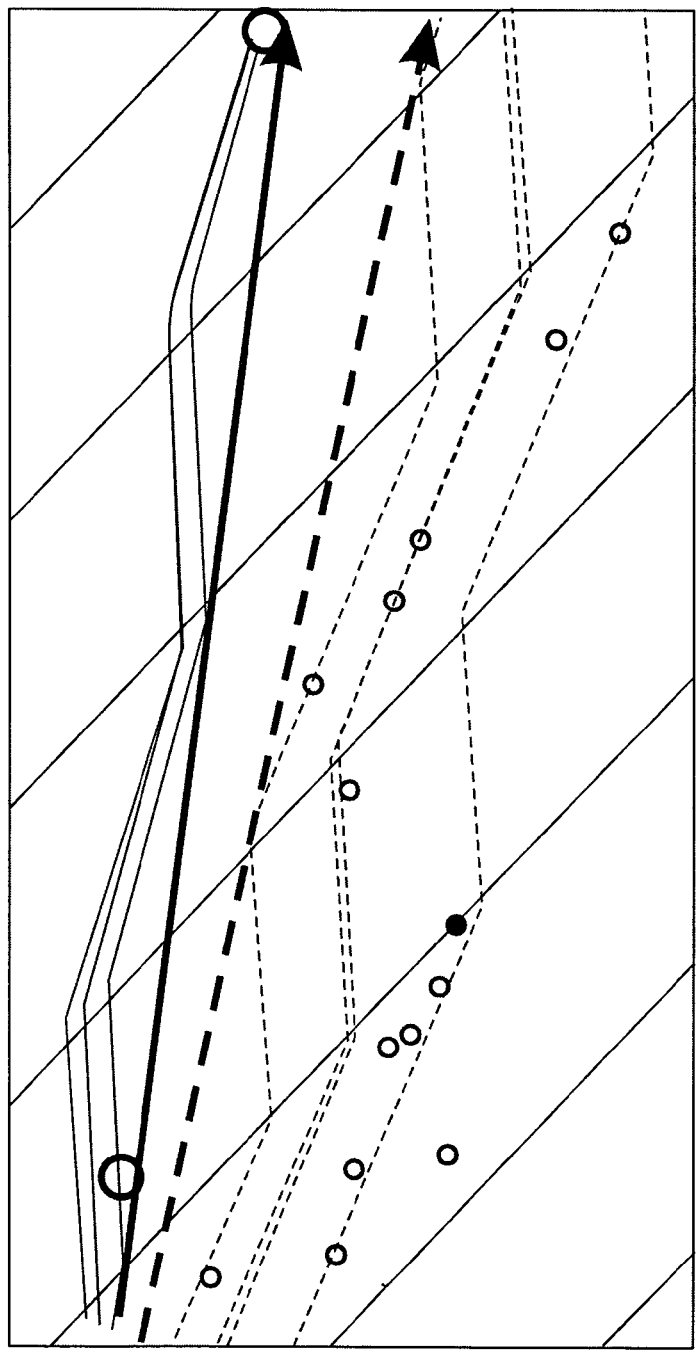
FIG. 14: illustrates trajectories of 10.11 (dotted lines) and 20.9 µm (solid lines) PS particles.

In addition, the deflection angles are clearly different for PS particles of different size, thus enabling their separation. FIG. 14 shows that the PS particles move in the direction of the main flow when they are on top of the ridges but are deflected as they traverse the cavities, which is consistent with general features observed in the particle free flow field. Interestingly, for all the PS particles the deflection angle is nearly constant as a function of the flow velocity, which indicates that particle sedimentation into the open cavities is not important for the range of velocities considered here. The figure also shows that the average deflection decreases as the particle size increases, also indicating that sedimentation effects are negligible for these lighter particles. Their deflection is in fact determined by the extent to which they are carried into the cavity by the flow.

FIG. 14 illustrates trajectories of 10.11 (dotted lines) and 20.9 µm (solid lines) PS particles as they traverse the large ridges (the arrows represent mean migration directions). The particles move in the direction of the main flow when they are on top of the ridges but are deflected as they traverse the cavities. This behavior is representative of what is observed for any particle that traverses the cavities in either geometry. Note the larger lateral displacement experienced by the smaller particles.

It is also observed that the small silica particles moving along the open cavities and close to the bottom wall, also migrate laterally to equilibrium positions on either corner of the cavities. Specifically, those particles moving in the vicinity of the downstream or reentrant corner attain an equilibrium position of a few microns away from ridge. On the other hand, the particles that are moving along the upstream (or entrant) corner move in close proximity to the wall. This observation is consistent with the presence and characteristic size of corotating recirculating regions observed in both corners of the cavities for the particle-free flow.

FIG. 13(b) presents the deflection angles measured in the device with small ridges. The main difference with respect to the results discussed before is the fact that both sizes of silica particles are eventually able to move across the ridges as the flow rate increases. More important for separation purposes, there is a range of velocities for which the larger silica particles move across the ridges (with $\Delta\theta\_10°$) but the smaller silica particles remain confined and move along the cavities $\Delta\theta=\_45°$). This is probably due to the larger drag force that the fluid exerts on the larger particles. (We note that, even at the largest flow rates, a few of the small silica particles become initially confined inside the cavities as they flow into the patterned region of the surface. These particles remain confined during their motion through the observation area and were not included in the analysis). The PS particles exhibit analogous behavior to that observed in the experiments performed in the device with large ridges. In general, it is clear that particles of the same density deflect less the larger they are, whereas particles of the same size deflect more the heavier they are. The fact that the contribution of sedimentation to the deflection angle decreases significantly with flow rate but the effect of particle size is independent of particle velocity is manifested by the cross-over (observed as a function of flow rate) between the deflection of small PS particles and large silica ones. At lower velocities, the density and sedimentation of the heavier particles dominates and they deflect more than the PS particles, even in the absence of total confinement. On the other hand, at higher velocities, sedimentation into the cavities becomes negligible, and the small PS particles deflect more than the larger silica ones.

Figure 16:
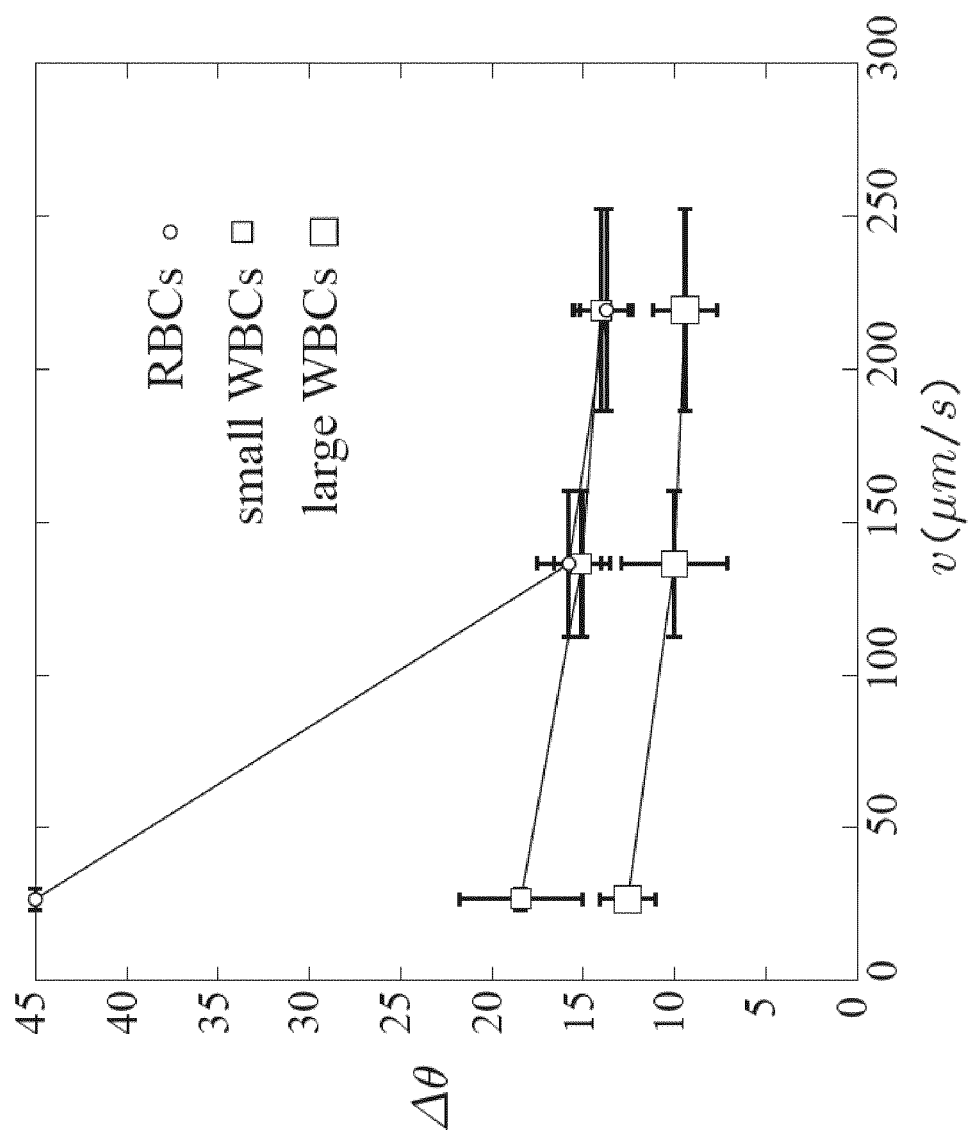
FIG. 16: Deflection angle of white and red blood cells (WBCs and RBCs) as a function of the approach velocity of the RBCs in the plain region of the device before the patterned area.

Next, a device with large ridges was used to demonstrate the potential of this platform to separate different cell populations present in a blood sample based on cell size and density. Specifically, red blood cells (RBCs), are smaller and heavier, and should therefore deflect more than white blood cells (WBCs). (Platelets are the smallest cellular components in blood, with densities in the range spanned by that of WBCs). In FIG. 16 the deflection angle for RBCs and WBCs as a function of flow rate is presented. In this case, the average velocity of RBCs in the flat region before they reach the patterned surface to characterize the flow velocity is used. It is clear that the dependence of the deflection angle of RBCs and WBCs on flow rate is qualitatively similar to the measurements performed with spherical particles, with the behavior of RBCs and WBCs resembling that of the silica and PS particles, respectively. Note, however, that the comparison with particle experiments is not quantitative, due to the substantial difference in density between RBCs and silica particles. As expected, RBCs deflect more than WBCs, and exhibit complete confinement inside the cavities at low flow rates. However, unlike the silica particles (in the experiments performed in the device with large ridges), RBCs can go over the ridges and move over the patterned surface as the flow rate increases, consistent with the fact that they are lighter than silica particles. Two subpopulations of WBCs could be clearly distinguished in the experiments. Larger WBCs deflect to a lesser extent than smaller ones. As in the case of the PS particles, the deflection angle of WBCs does not change considerably over the range of velocities considered, which indicates that sedimentation does not play a role in their behavior. Platelets remain suspended across the height of the channel and thus, because of their small size and light buoyant weight, they serve as tracer particles to interrogate the flow. Platelets exhibited abroad range of deflection angles depending on their vertical position, with those moving far from the bottom surface not deflecting at all, and those that moved close to the patterned surface showing the largest deflection angles (for simplicity, their deflection angle was not included in FIG. 16). In fact, the streams of platelets that did not deflect at all were collected with 100% purity in the outlet channel aligned with the injection channel used to flow focus the cells into the device. These observations are also consistent with the characteristics of the particle free flow, and confirm that the effect of the patterned surface on the flow is localized to its vicinity and that the recirculation observed in confined geometries is negligible here.

Figure 15:
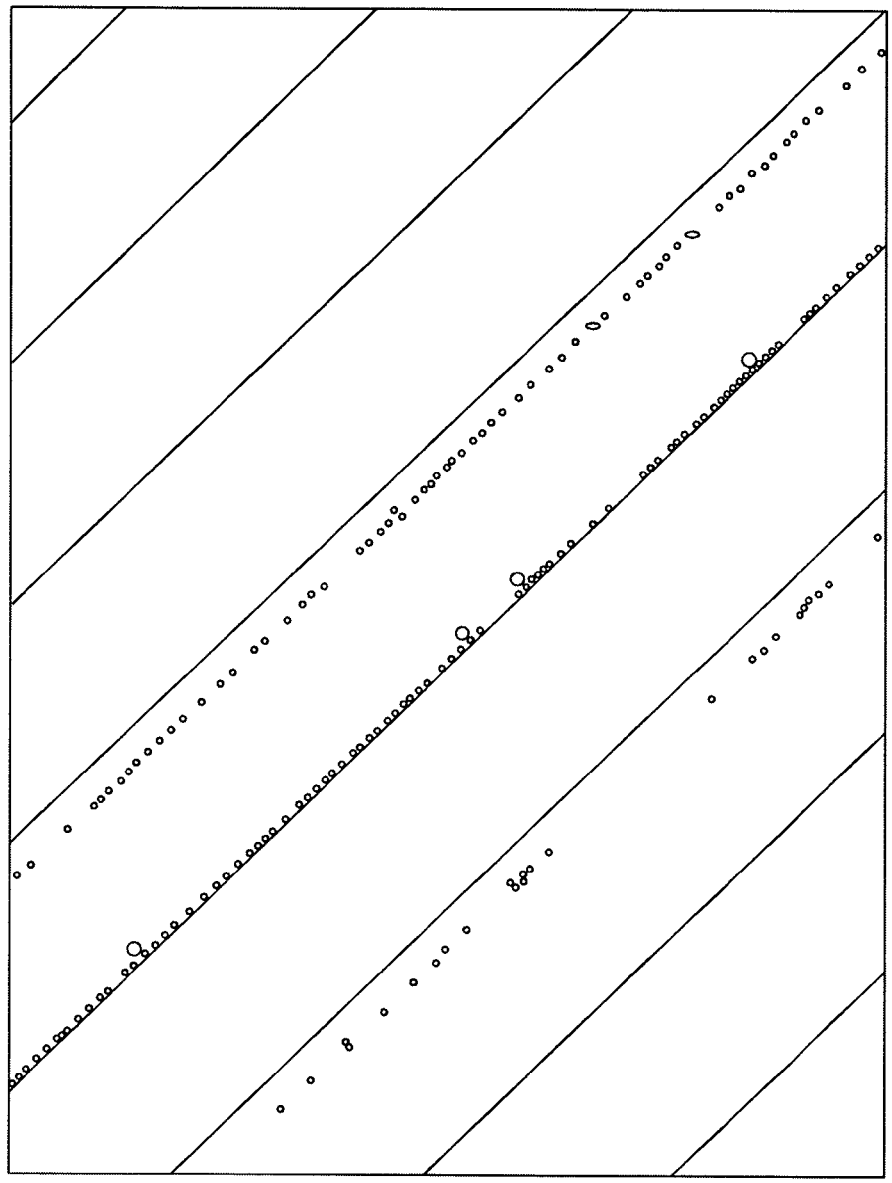
FIG. 15: illustrates trajectories of 4.31 µm silica particles.

FIG. 15 illustrates trajectories of 4.31 μm silica particles. They are confined to flow along the cavities in the device with large ridges. Particles moving in the vicinity of the downstream or reentrant corner attain an equilibrium position of a few microns away from ridge, while those moving along the upstream (or entrant) corner move in close proximity to the wall. This behavior is consistent with the presence and characteristic size of the corotating recirculating regions observed in the particle-free flow. A few of the 10 μm PS particles were also caught in the upstream recirculating region as they first entered the cavities.

Scope & Applicability

In general, this invention allows the sorting and focusing of suspended particles, biological and otherwise, based on their sedimentation velocity. The characteristics of the flow along the grooves can be tuned by changing geometrical parameters including the groove depth relative to the channel height, the width of the grooves and steps relative to channel width, the topography of the transition between the grooves and the steps, the shape of the path along the grooves (e.g., sinusoidal stripes) and their orientation with respect to the channel. Particular dimensions depend of the specific application and can span the nano and micro-scale. Several applications are envisioned, broadly categorized as the continuous separation of: biological cells, non-biological particles and droplets, and bio-molecules.

Passive Separation of Biological Cells:

Blood Fractionation:

This invention allows the mild and nondestructive depletion and recovery of RBCs from the rest of the blood components with high purity serving as an alternative to centrifugation and chemical lysis. Furthermore, plasma proteins, bacteria, platelets, different subpopulations of WBCs, and other rare blood cells migrate at different angles and can be continuously collected.

Separation of Different Subpopulations from Digested Tissue:

Another application is the separation of cells from digested tissue based on their size, mass, shape, and stiffness, all factors affecting their settling velocity. Currently this is done by filtering which is prone to clogging and contamination.

Passive Separation of Non-Biological Particles and Droplets:

Droplets and particles (silica, polymeric, metallic, etc.), which are routinely used in many applications, can also be separated based on their size, mass, shape and stiffness.

Separation of Cells and Biomolecules Using External Fields:

The separation of cells, proteins, RNA and DNA can also be performed using centrifugal, electric, dielectrophoretic and magnetic forces perpendicular to the patterned substrate to selectively confined different species along the grooves for different periods of time causing them to migrate at different angles.

Separation of Tagged Cells and Biomolecules Using External Fields:

Particular cells and bio-molecules can be tagged with particles via specific marker-antibody interactions to increase their settling velocity to allow their isolation. The tagging particles can be chosen to be heavy to use earth's gravitational field or centrifugation to increase the settling velocity of the tagged target. Alternatively, the charge, dielectric, magnetic, and optical properties of the tags can be chosen to use an electric, dielectrophoretic or magnetic field to also increase the settling velocity of the complexes. Particular examples include the isolation of proteins, RNA and DNA, bacteria, leukocytes, and rare blood cells like circulating tumor cells.

It will be appreciated to the skilled person that the flow-field generated by the channel and its grooves exerts different forces on different types of particles which are flowing in the channel, for instance for particle types having different sedimentation or settling velocity. At the same time it should be understood that due to the nature of the field of the present invention, namely (micro) fluidic channels and particles and flows thereof, the findings and effects of the device and methods can be applicable to most of the particles of the same type, but statistical deviations are possible. Therefore, when a behavior or effect of the device or method according to a the present invention on a type of particles is mentioned in the description above, it may relate to or be applicable to or have effect on for instance 90%, or 95%, or 99% or 99.9%, or 9.99%, or 99.999% of that type of particles.

In general, different fields can be used to control the height of different particles. Particles can be forced to sample a desired region of the reorienting flow. As mentioned before, external fields can play or enhance the role of gravity to pull particle into the grooves. Similarly, external fields can be used to push particles out of the cavities, thereby reducing their deflection.

Differences in settling velocity can also be used to control the time of arrival of different species to a ridged surface. In this case, particles of the same or different size but with different settling velocity would eventually separate laterally after reaching the patterned surface at different times, even if sedimentation does not play a role in their migration angle.

Whenever the word "means for" is used this can refer for instance to a device for, an apparatus for or a system for.

Definition of Cross-Sectional Flow Regimes

Figure 2:
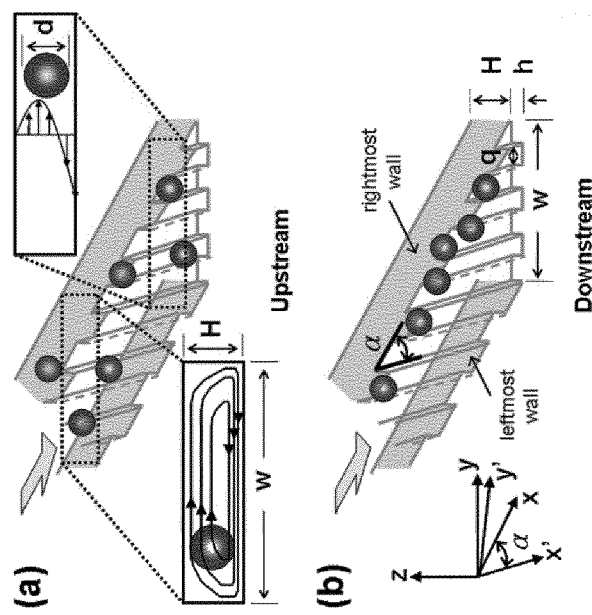
FIG. 2: (prior art) Enrichment of particles by size in confined devices.
Figure 3:
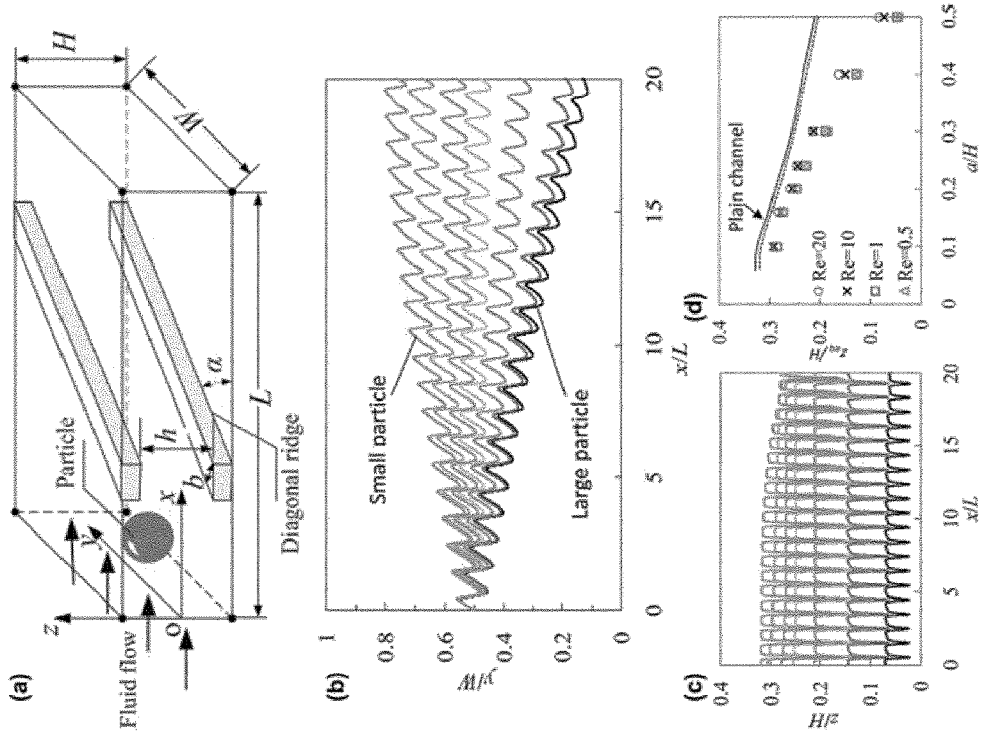
FIG. 3: (prior art) Size based separation of neutrally buoyant spherical particles.

In a closed channel with periodic slanted trenches, the flow circulates in the cross-sectional plane, as shown in FIG. 2 (a). Because of the slanted trenches, the flow very close to the ridges, i.e. the surface flow, tends to flow along the ridges resulting a flow rate Vx>0. When the cross-sectional flow reaches the fluidic channel side wall (the leftmost wall in FIG. 2), it flows upwards and backwards to the other side wall (the right most wall in FIG. 2) to complete the circulation (Vx<0), i.e. the recirculation flow. A particle is subjected to the surface flow if its vertical position z<$H_0$, and to the recirculation flow if $z>H_0$. The latter situation was exploited by the prior art, and the former situation is described in embodiments of the present invention. The prior art uses slanted ridges to create recirculation in the channel cross-section while, in an embodiment of the invention, slated open grooves, i.e. grooves which are open-ended, are used that guide flow along them but otherwise leave the flow unaffected.

Impact of Flow Rate to the Device Performance.

Laminar flow is stongly preferred for separation mechanisms according to embodiments of the present invention. Thus, the flow rate needs to be low enough. Preferably the i Reynolds number is thereby restricted, preferably Re<1000, more preferably Re<100. With laminar flow, the side-based separation is effective as long as h, the ridge height, and R, the particle radius, becomes comparable, preferably h>R. Except for the laminar flow, the flow rate for the size-based separation is not limited by other conditions.

Figure 17:
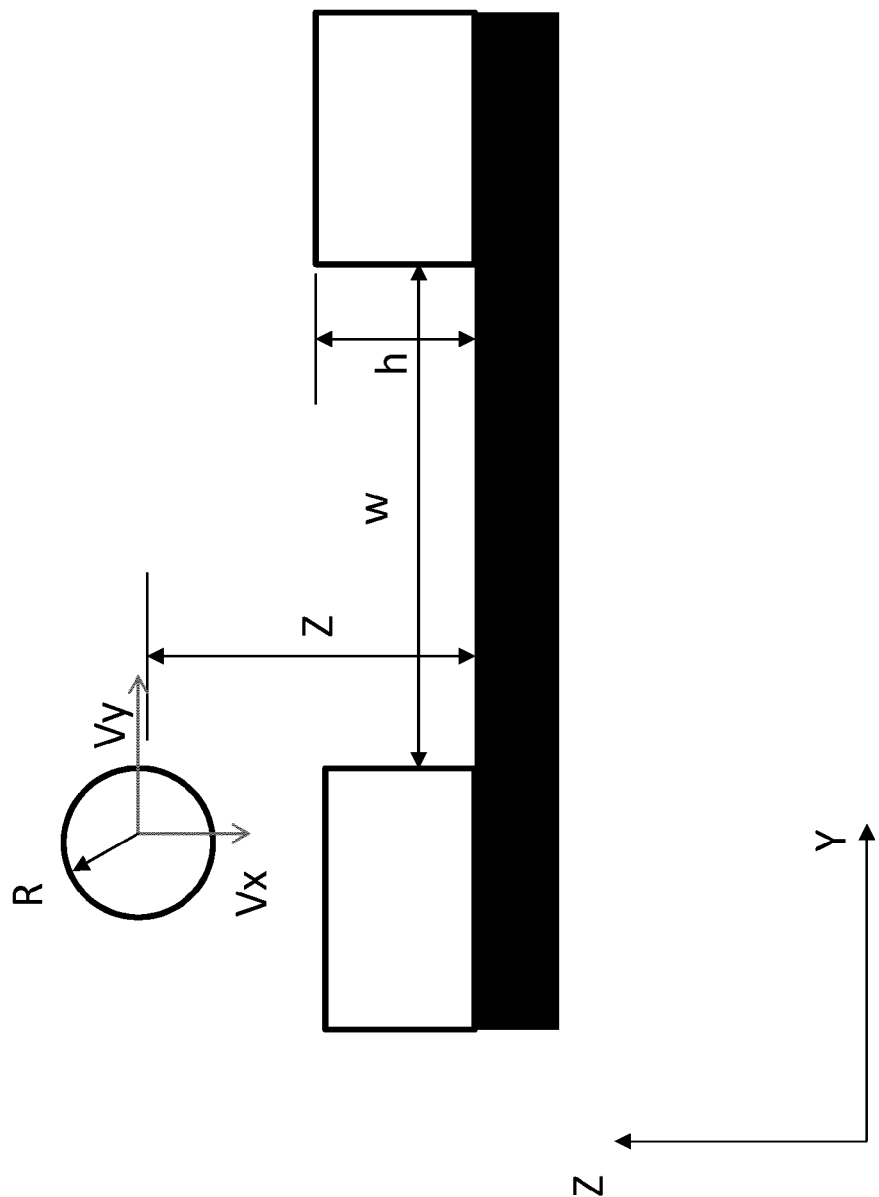
FIG. 17: Illustrates a model used to define cross-sectional flow regimes and model the Impact of flow rate to the device performance.

For sedimentation-based separation, however, the flow rate $V_y$ needs to be sufficiently low in order to allow particle sedimentation into the trench. Equation A1 gives a magnitude estimation of the maximum $V_y$ for the sedimentation-based separation, in which w is trench width and τ is the time for a full sedimentation from the top of the ridge to the bottom of the trench (also refer to FIG. 17). The time τ can also be calculated by Eq. A2 if a constant velocity (i.e. normally named "terminal velocity" in literature, Eq. A3) is assumed for particle sedimentation in the Z direction, where h is the trench depth, $\rho_p$ the particle density, $\rho_m$ the medium density, $V_p$ the particle volume, R the particle radius and η the dynamic viscosity of the medium.

$$V_y = w/\tau \quad (Eq. A1)$$

$$\tau = h/V_t \quad (Eq. A2)$$

$$V_t = [(\rho_p - \rho_p) * g * V_p] / [6\pi * R * \eta] \quad (Eq. A3)$$

The invention claimed is:

1. A micro-fluidic device for sorting particles in a liquid sample, the device comprising
a micro-fluidic channel comprising a particle separation region comprising an array of grooves, the grooves being oriented at an angle in the range of 20 degrees to 70 degrees with respect to a main axis of the channel;
a means for injecting the liquid sample into said micro-fluidic channel;
a means for collecting particles whereby the means for injecting the liquid sample and the means for collecting particles are interconnected via the micro-fluidic channel; and
the liquid sample comprising the particles to be sorted, the liquid sample being disposed within the micro-fluidic channel,
wherein the dimensions of the micro-fluidic channel are considerably larger than the dimensions of the grooves to prevent confinement effects, the height of the micro-fluidic channel being at least five times the depth of the grooves, the micro-fluidic channel being configured to avoid recirculation effects inside the micro-fluidic channel, and
wherein the width and spacing between the grooves is at least 2 times the size of the particles to be sorted.

2. A micro-fluidic device according to claim 1, wherein the array of grooves is partly patterned at the bottom surface of the micro-fluidic channel such that the bottom surface of the micro-fluidic channel comprises a non-patterned part, and wherein the non-patterned part of the bottom surface is configured to flow-focus the stream of particles.

3. A micro-fluidic device according to claim 1, wherein the height of the micro-fluidic channel is at least 10 times the depth of the grooves.

4. A micro-fluidic device according to claim 1, wherein said grooves are open-ended.

5. A micro-fluidic device according to claim 1, wherein the width of the channel is at least 50 times the width of the grooves.

6. A micro-fluidic device according to claim 1, wherein the depth of each groove of the array of grooves is at least the size of the particles to be sorted.

7. A micro-fluidic device according to claim 1, wherein the width and spacing between the grooves is at least 10 times the size of the particles to be sorted.

8. A micro-fluidic device according to claim 1, wherein the array of grooves are slanted and patterned at the bottom of the surface of the micro-fluidic channel.

9. A micro-fluidic device according to claim 1, wherein the means for injecting the liquid sample into to the micro-fluidic channel does so in a flow-focused manner.

10. A micro-fluidic device according to claim 1, wherein the means for injecting the liquid sample comprises at least one inlet.

11. A micro-fluidic device according to claim 1, wherein the means for injecting the liquid sample comprises an inlet and one or more micro-fluidic channels.

12. A micro-fluidic device according to claim 1, wherein the means for collecting particles are one or more micro-fluidic channels, the channels being arranged to prevent recombining the segregated streams.

13. A micro-fluidic device according to claim 12, wherein the channels are evenly spaced, thereby ensuring that they have the same hydrodynamic resistance.

14. A micro-fluidic device according to claim 1, further comprising a sedimentation region arranged to let particles partly sediment in order to diminish recirculation effects on the particles present above the array of grooves.

15. A method for sorting particles in a liquid sample with a device according to claim 1, the method comprising injecting the liquid sample into the micro-fluidic channel such that the liquid sample comprising the particles to be sorted is disposed within the micro-fluidic channel, separating the particles with the separation region and capturing streams of different particles with the means for collecting particles.

16. A method according to claim 15, wherein injecting the liquid sample into the micro-channel is performed in a flow focused manner.

17. A method according to claim 15, further comprising allowing the sedimentation of the particles in said liquid sample before injecting the liquid sample into the micro-fluidic channel.

18. A method according to claim 15, the method further comprising adjusting focusing and sample injection flow of one or more micro-fluidic channels for focusing the flow of particles.

19. A method for sorting particles in a liquid sample with a device according to claim 1, comprising flowing the liquid sample comprising the particles to be sorted in the micro-fluidic channel at an average velocity which is comparable to the sedimentation velocity of said particles.

20. A method for sorting particles in a liquid sample with a device according to claim 1, comprising flowing the liquid sample comprising the particles to be sorted in the microfluidic channel at an average velocity which is substantially larger than the sedimentation velocity of said particles.

21. A micro-fluidic device according to claim 1, wherein the width and spacing between the grooves is at least 5 times the size of particles to be sorted.

22. A micro-fluidic device according to claim 1, wherein the array of grooves is fully-patterned at the bottom surface of the micro-fluidic channel.

23. A micro-fluidic device according to claim 1, wherein
  the width and spacing between the grooves is at least 5 times the size of particles to be sorted; and
  the depth of each groove of the array of grooves is at least the size of the particles to be sorted.

24. A method for sorting particles in a liquid sample with a device according to claim 23, the method comprising injecting the liquid sample comprising the particles to be sorted into the micro-fluidic channel, separating the particles with the separation region and capturing streams of different particles with the means for collecting particles.

* * * * *